United States Patent

Lindquist

[11] Patent Number: 6,006,798
[45] Date of Patent: Dec. 28, 1999

[54] SYRINGE LOADING JIG

[76] Inventor: Barbara J. Lindquist, 747 Marcy St., Ottawa, Ill. 61350

[21] Appl. No.: 09/169,105

[22] Filed: Oct. 9, 1998

[51] Int. Cl.$^6$ ....................................................... B65B 1/04
[52] U.S. Cl. .............................. 141/27; 141/25; 141/231; 141/232; 141/369; 141/375; 604/414; 128/919
[58] Field of Search ................................. 141/18, 21, 25, 141/27, 231, 232, 311 R, 318, 328, 369, 375; 222/309; 604/407, 414, 905; 128/919

[56] References Cited

U.S. PATENT DOCUMENTS

| | | | |
|---|---|---|---|
| 3,840,011 | 10/1974 | Wright | 128/272 |
| 4,219,055 | 8/1980 | Wright | 141/27 |
| 4,489,766 | 12/1984 | Montada | 141/27 |
| 4,778,454 | 10/1988 | La Dow | 604/208 |
| 5,377,725 | 1/1995 | Neff | 141/27 |
| 5,468,233 | 11/1995 | Schraga | 604/207 |
| 5,487,738 | 1/1996 | Sciulli | 604/414 |
| 5,873,859 | 2/1999 | Muntz | 604/207 |
| 5,894,870 | 4/1999 | Maxwell | 141/27 |

*Primary Examiner*—Henry J. Recla
*Assistant Examiner*—Timothy L. Maust
*Attorney, Agent, or Firm*—Joseph N. Breaux

[57] ABSTRACT

A syringe loading jig that includes structures for gripping and holding a medicant vial in concentric alignment with a syringe and includes a horizontal fastening mechanism for securing the syringe loading jig to a horizontal surface and a vertical fastening mechanism for securing the syringe loading jig to a vertical surface. The syringe loading jig includes a resilient molded jig structure forming a vial holding assembly and a syringe holding assembly. The vial holding assembly includes a lockable vial securing clip and a resilient vial body receiving cavity, a vial neck receiving channel and a vial cap receiving cavity. The resilient vial body receiving cavity, the vial neck receiving channel and the vial cap receiving cavity are concentrically aligned. The syringe holding assembly includes a syringe securing clip and a resilient open-ended and open-topped syringe body receiving channel concentrically aligned with the resilient vial body receiving cavity, the vial neck receiving channel and the vial cap receiving cavity of the vial holding assembly. The resilient molded jig structure has a finger insertion opening formed therein in connection with the resilient vial body receiving cavity, a back surface provided with a jig back surface fastening mechanism, and a vial end surface provided with jig vial end fastening mechanism.

2 Claims, 2 Drawing Sheets

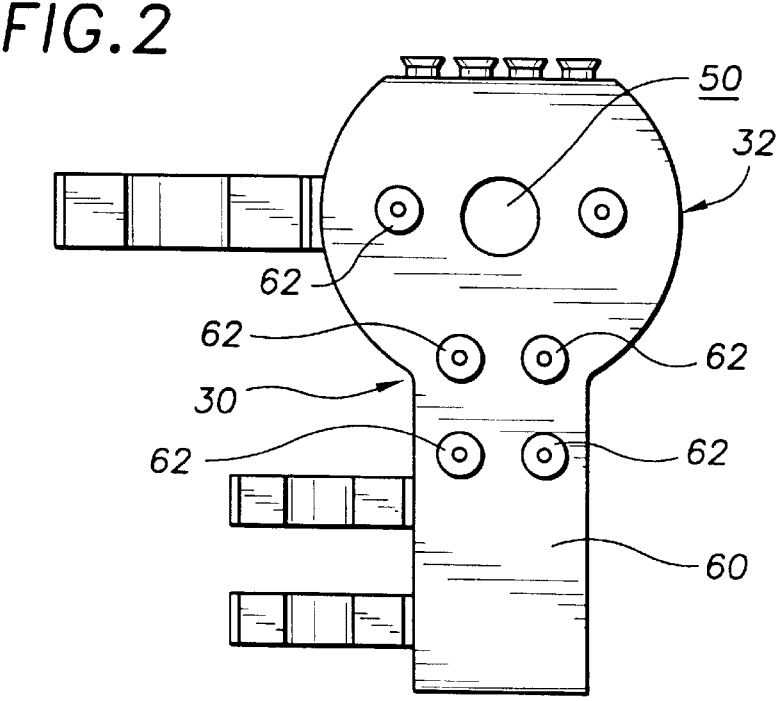
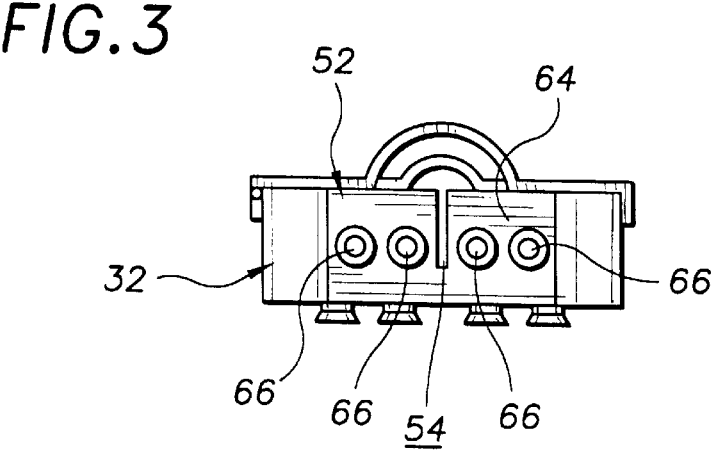
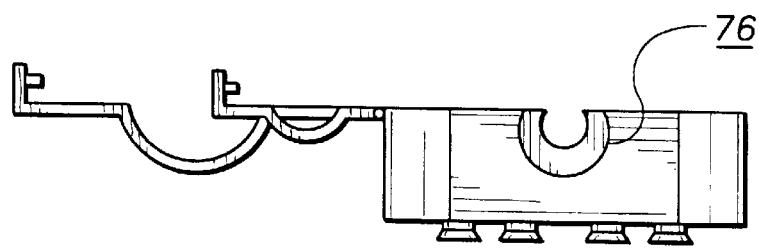

SYRINGE LOADING JIG

TECHNICAL FIELD

The present invention relates to devices for assisting in loading a syringe from a medicine vial and more particularly to a syringe loading jig including a resilient molded jig structure forming a vial holding assembly and a syringe holding assembly; the vial holding assembly including a lockable vial securing clip and a resilient vial body receiving cavity, a vial neck receiving channel and a vial cap receiving cavity; the resilient vial body receiving cavity, the vial neck receiving channel and the vial cap receiving cavity being concentrically aligned; the vial receiving clip being lockable in a position across a vial cavity access opening; the syringe holding assembly including a syringe securing clip and a resilient open-ended and open-topped syringe body receiving channel concentrically aligned with the resilient vial body receiving cavity, the vial neck receiving channel and the vial cap receiving cavity of the vial holding assembly; the resilient molded jig structure having a finger insertion opening formed therein in connection width the resilient vial body receiving cavity; the resilient molded jig structure having a back surface provided with a jig back surface fastening mechanism and a vial end surface provided with jig vial end fastening mechanism; the vial end of the resilient molded jig structure having an expansion slit formed therethrough in connection with the vial body receiving cavity to provide sufficient expansion of the vial body receiving cavity to receive and grip therein the vial body of a medicant vial; the syringe body receiving channel having a semi-circular cross section describing an arc greater than two-hundred degrees.

BACKGROUND ART

It is often difficult for individuals with the use of a single arm and hand to accurately fill a syringe with a proper dose of insulin or other self administered medicant. It would be a benefit to these individuals to have a syringe loading jig that could be used to grip and hold the medicant vial in concentric alignment with a syringe so that one hand could be used to adjust the plunger handle of the syringe to draw the proper medicant dose into the syringe body of the syringe without the need for simultaneously physically gripping the medicant visal and the syringe plunger. In addition, because it can be difficult to position the plunger when the syringe loading jig is free to move, it would be a further benefit to have a syringe loading jig that included at least one fastening mechanism for fastening the jig to a fixed surface. Because it could be desirable to secure the syringe loading jig to either a horizontal or a vertical surface, it would also be a benefit to have a horizontal fastening mechanism for securing the syringe loading jig to a horizontal surface and a vertical fastening mechanism for securing the syringe loading jig to a vertical surface.

GENERAL SUMMARY DISCUSSION OF INVENTION

It is thus an object of the invention to provide a syringe loading jig that includes structures for gripping and holding a medicant vial in concentric alignment with a syringe.

It is a further object of the invention to provide a syringe loading jig that includes a fastening mechanism for fastening the jig to a fixed surface.

It is a still further object of the invention to provide a syringe loading jig that includes a horizontal fastening mechanism for securing the syringe loading jig to a horizontal surface and a vertical fastening mechanism for securing the syringe loading jig to a vertical surface.

It is a still further object of the invention to provide a syringe loading jig that includes a resilient molded jig structure forming a vial holding assembly and a syringe holding assembly; the vial holding assembly including a lockable vial securing clip and a resilient via body receiving cavity, a vial neck receiving channel and a vial cap receiving cavity; the resilient vial body receiving cavity, the vial neck receiving channel and the vial cap receiving cavity being concentrically aligned; the vial receiving clip being lockable in a position across a vial cavity access opening; the syringe holding assembly including a syringe securing clip arid a resilient open-ended and open-topped syringe body receiving channel concentrically aligned with the resilient vial body receiving cavity, the vial neck receiving channel and the vial cap receiving cavity of the vial holding assembly; the resilient molded jig structure having a finger insertion opening formed therein in connection with the resilient vial body receiving cavity; the resilient molded jig structure having a back surface provided with a jig back surface fastening mechanism and a vial end surface provided with jig vial end fastening mechanism; the vial end of the resilient molded jig structure having an expansion slit formed therethrough in connection with the vial body receiving cavity to provide sufficient expansion of the vial body receiving cavity to receive arid grip therein the vial body of a medicant vial; the syringe body receiving channel having a semi-circular cross section describing an arc greater than two-hundred degrees.

It is a still further object of the invention to provide a syringe loading jig that accomplishes some or all of the above objects in combination.

Accordingly, a syringe loading jig is provided. The syringe loading jig includes a resilient molded jig structure forming a vial holding assembly and a syringe holding assembly; the vial holding assembly including a lockable vial securing clip and a resilient vial body receiving cavity, a vial neck receiving channel and a vial cap receiving cavity; the resilient vial body receiving cavity, the vial neck receiving channel and the vial cap receiving cavity being concentrically aligned; the vial receiving clip being lockable in a position across a vial cavity access opening; the syringe holding assembly including a syringe securing clip and a resilient open-ended and open-topped syringe body receiving channel concentrically aligned with the resilient vial body receiving cavity, the vial neck receiving channel and the vial cap receiving cavity of the vial holding assembly; the resilient molded jig structure having a finger insertion opening formed therein in connection with the resilient vial body receiving cavity; the resilient molded jig structure having a back surface provided with a jig back surface fastening mechanism and a vial end surface provided with jig vial end fastening mechanism; the vial end of the resilient molded jig structure having an expansion slit formed therethrough in connection with the vial body receiving cavity to provide sufficient expansion of the vial body receiving cavity to receive and grip therein the vial body of a medicant vial; the syringe body receiving channel having a semi-circular cross section describing an arc greater than two-hundred degrees.

BRIEF DESCRIPTION OF DRAWINGS

For a further understanding of the nature and objects of the present invention, reference should be made to the following detailed description, taken in conjunction with the accompanying drawings, in which like elements are given the same or analogous reference numbers and wherein:

FIG. 2 is a underside plan view of the resilient molded jig structure showing the finger insertion opening used to eject medicant vials from the resilient vial body receiving cavity; the six back surface attachment suction cups; and the four vial end surface attachment suction cups.

FIG. 3 is plan view of the vial end of the syringe loading jig of FIG. 1 showing the expansion slit formed through the vial end of the resilient molded jig structure in connection with the vial body receiving cavity to provide sufficient expansion of the vial body receiving cavity to receive and grip therein the vial body of a medicant vial; the vial securing clip in the closed position; the two syringe securing clips in the closed position; four of the six back surface attachment suction cups; and the four vial end surface attachment suction cups.

FIG. 4 is a plan view of the syringe insertion end of syringe loading jig of FIG. 1 showing the open-ended resilient, semi-circular, syringe body receiving channel concentrically aligned with the resilient vial body receiving cavity, the semi-circular, syringe body receiving channel describing an arc greater than two-hundred degrees.

EXEMPLARY MODE FOR CARRYING OUT THE INVENTION

Figure 1:
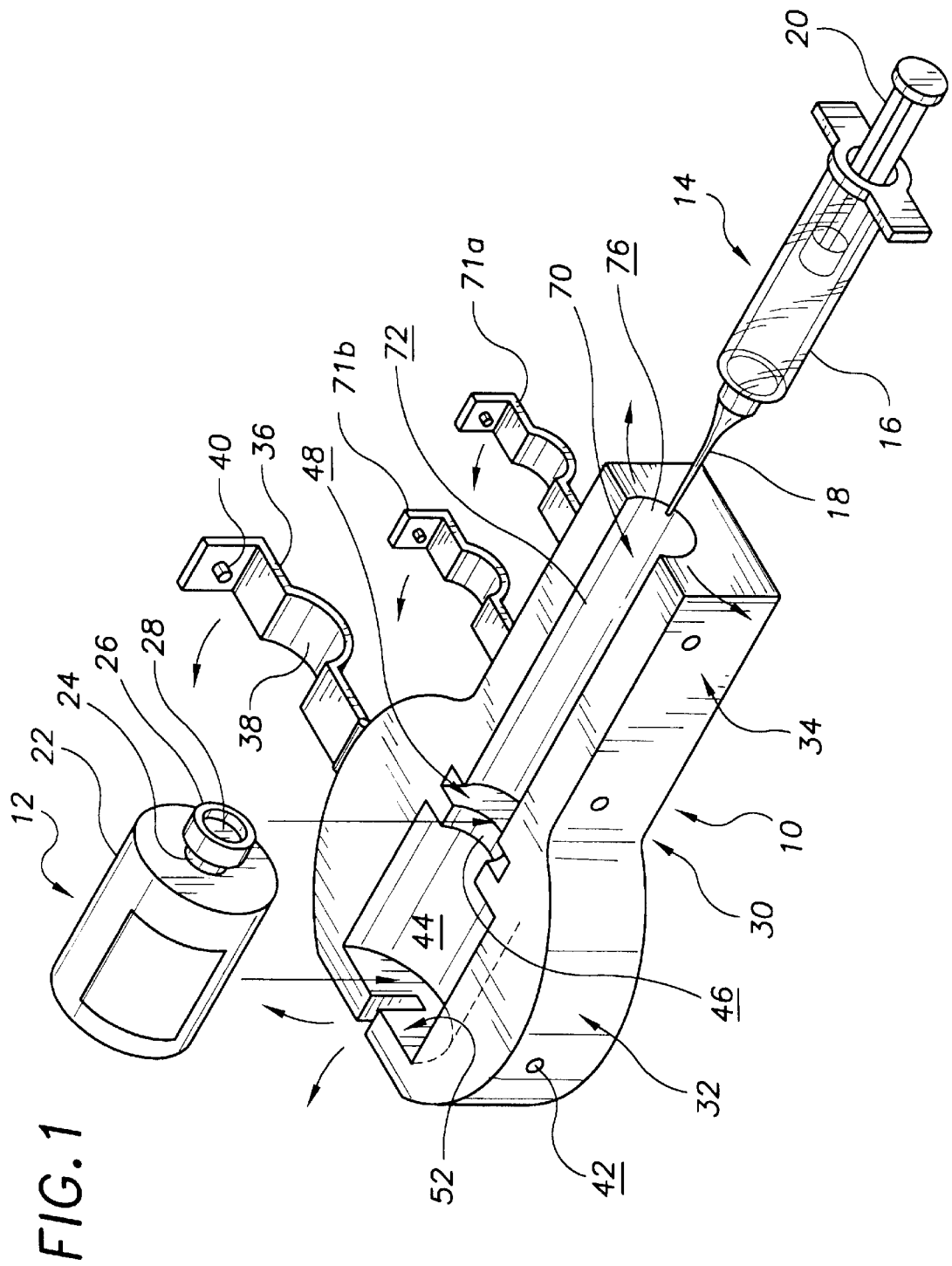
FIG. 1 is a perspective view of an exemplary embodiment of the syringe loading jig of the present invention along with a representative medicant insulin vial and insulin syringe showing the resilient molded jig structure including the vial holding assembly including the vial securing clip and the concentrically aligned resilient vial body receiving cavity, vial neck receiving channel and vial cap receiving cavity; and the syringe holding assembly including the two syringe securing clips and the resilient syringe body receiving channel concentrically aligned with the resilient vial body receiving cavity, vial neck receiving channel and vial cap receiving cavity of the vial holding assembly.

FIG. 1 shows an exemplary embodiment of the syringe loading jig of the present invention, generally designated by the numeral 10, along with a representative insulin vial, generally designated 12, and a representative insulin syringe, generally designated 14. Insulin syringe 14 includes a cylindrical syringe body 16, a syringe needle 18, and a syringe plunger 20. Insulin vial 12 includes a cylinder shaped vial body 22, a vial neck 24, and a vial cap 26. Vial cap 26 has a punctureable membrane 28 through which syringe needle 18 is inserted to withdraw the insulin from vial body 22 into syringe body 16.

Syringe loading jig 10 includes a resilient molded jig structure, generally designated 30, including a vial holding assembly, generally designated 32, and a syringe holding assembly, generally designated 34. Vial holding assembly 32 includes a pivoting vial securing clip 36 and a resilient vial body receiving cavity 44, vial neck receiving channel 46 and vial cap receiving cavity 48. Vial securing clip 36 is integrally molded with jig structure 30 arid includes a contoured vial body contact portion 38 and a securing pin 40 that is insertable into a pin receiving aperture 42.

With reference to FIG. 2, vial holding assembly 32 also includes a finger insertion opening 50 that is used to eject an insulin vial 12 (FIG. 1) from resilient vial body receiving cavity 44 (FIG. 1). With reference to FIG. 3, vial holding assembly 32 further includes a vial end 52 (see also FIG. 1) that has an expansion slit 54 formed therethrough in connection with vial body receiving cavity 44 (FIG. 1) to provide sufficient expansion of the vial body receiving cavity 44 (FIG. 1) to receive and grip therein vial body 22 of insulin vial 12.

Referring back to FIG. 2, jig structure 30 has a back surface 60 upon which are provided six back surface attachment suction cups 62 that are used to attach jig structure 30 to a suitable surface. Similarly, referring back to FIG. 3, jig structure 30 has a vial end surface 64 upon which are provided four vial end surface attachment suction cups 66 that are also used to attach jig structure 30 to a suitable surface.

Referring back to FIG. 1, syringe holding assembly 34 has an elongated, open-ended, resilient, semi-circular, syringe body receiving channel 70 and two integrally molded syringe securing clips 71a, 71b. Syringe body receiving channel 70 is concentrically aligned with resilient vial body receiving cavity 44 and has a rectangular top opening 72 and a semi-circular side opening 76. Referring to FIG. 4, semi-circular side opening 76 describes an arc of two-hundred-twenty degrees.

With general reference to FIGS. 1–4, in use jig structure 30 is attached in place to a suitable structure using back surface attachment suction cups 62 or vial end surface attachment suction cups 66. Once jig structure 30 is secured in place, a medicant vial, such as insulin vial 12, is snap fit into vial holding assembly 32 and secured with vial securing clip 36. Cylindrical syringe body 16 is then inserted into syringe body receiving channel 70 of syringe holding assembly 34 through semi-circular side opening 76 such that syringe needle 18 punctures punctureable membrane 28 of insulin vial 12. Syringe 14 is then secured in place with syringe securing clips 71a, 71b. When in the closed position, syringe securing clips 71a, 71b compress syringe holding assembly 34 causing the wails defining syringe body receiving channel 70 to grip syringe body 16 and prevent slippage of syringe body 16 with respect to insulin vial 12. The user can then position syringe plunger 20 to the desired position to withdraw the required medicant, such as an insulin dose, into syringe body 16.

It can be seen from the preceding description that a syringe loading jig has been provided that includes structures for gripping and holding a medicant vial in concentric alignment with a syringe; that includes a fastening mechanism for fastening the jig to a fixed surface; that includes a horizontal fastening mechanism for securing the syringe loading jig to a horizontal surface and a vertical fastening mechanism for securing the syringe loading jig to a vertical surface; and that includes a resilient molded jig structure forming a vial holding assembly and a syringe holding assembly; the vial holding assembly including a lockable vial securing clip and a resilient vial body receiving cavity, a vial neck receiving channel and a vial cap receiving cavity; the resilient vial body receiving cavity, the vial neck receiving channel and the vial cap receiving cavity being concentrically aligned; the vial receiving clip being lockable in a position across a vial cavity access opening; the syringe holding assembly including a syringe securing clip and a resilient open-ended and open-topped syringe body receiving channel concentrically aligned with the resilient vial body receiving cavity, the vial neck receiving channel and the vial cap receiving cavity of the vial holding assembly; the resilient molded jig structure having a finger insertion opening formed therein in connection with the resilient vial body receiving cavity; the resilient molded jig structure having a back surface provided with a jig back surface fastening mechanism and a vial end surface provided with jig vial end fastening mechanism; the vial end of the resilient molded jig stricture having an expansion slit formed therethrough in connection with the vial body receiving cavity to provide sufficient expansion of the vial body receiving cavity to receive and grip therein the vial body of a medicant vial; the syringe body receiving channel having a semi-circular cross section describing an arc greater than two-hundred degrees.

It is noted that the embodiment of the syringe loading jig described herein in detail for exemplary purposes is, of course, subject to many different variations in structure, design, application and methodology. Because many varying and different embodiments may be made within the scope of the inventive concept(s) herein taught, and because many modifications may be made in the embodiment herein detailed in accordance with the descriptive requirements of the law, it is to be understood that the details herein are to be interpreted as illustrative and not in a limiting sense.

What is claimed is:

1. A syringe loading jig comprising:

a resilient molded jig structure forming a vial holding assembly and a syringe holding assembly;

said vial holding assembly including a lockable vial securing clip and a resilient vial body receiving cavity, a vial neck receiving channel and a vial cap receiving cavity;

said resilient vial body receiving cavity, said vial neck receiving channel and said vial cap receiving cavity being concentrically aligned;

said vial receiving clip being lockable in a position across a vial cavity access opening;

said syringe holding assembly including a syringe securing clip and a resilient open-ended and open-topped syringe body receiving channel concentrically aligned with said resilient vial body receiving cavity, said vial neck receiving channel and said vial cap receiving cavity of said vial holding assembly;

said resilient molded jig structure having a finger insertion opening formed therein in connection with said resilient vial body receiving cavity;

said resilient molded jig structure having a back surface provided with a jig back surface fastening mechanism and a vial end surface provided with jig vial end fastening mechanism;

said vial end of said resilient molded jig structure having an expansion slit formed therethrough in connection with said vial body receiving cavity to provide sufficient expansion of said vial body receiving cavity to receive and grip therein a vial body of a medicant vial;

said syringe body receiving channel having a semi-circular cross section describing an arc greater than two-hundred degrees.

2. The syringe loading jig of claim 1 wherein:

said jig back surface fastening mechanism is a suction cup and said jig vial end fastening mechanism is a suction cup.

* * * * *